(12) United States Patent
Confalone et al.

(10) Patent No.: US 8,785,714 B2
(45) Date of Patent: Jul. 22, 2014

(54) ALKALI NEUTRALIZING ACQUISITION AND DISTRIBUTION STRUCTURES FOR USE IN PERSONAL CARE ARTICLES

(75) Inventors: Philip Confalone, Raritan, NJ (US); Rajeev Farwaha, Belle Mead, NJ (US)

(73) Assignee: Celanese International Corporation, Irving, TX (US)

( * ) Notice: Subject to any disclaimer, the term of this patent is extended or adjusted under 35 U.S.C. 154(b) by 496 days.

(21) Appl. No.: 13/036,606

(22) Filed: Feb. 28, 2011

(65) Prior Publication Data

US 2012/0220968 A1 Aug. 30, 2012

(51) Int. Cl.
*A61F 13/15* (2006.01)
*B32B 27/04* (2006.01)

(52) U.S. Cl.
USPC ........... 604/359; 604/360; 604/367; 604/372; 442/149; 442/118

(58) Field of Classification Search
USPC .......... 604/360, 367, 359, 372; 442/374, 417, 442/118, 149
See application file for complete search history.

(56) References Cited

U.S. PATENT DOCUMENTS

| | | | |
|---|---|---|---|
| 4,657,537 A | 4/1987 | Zimmerer | |
| 4,902,564 A | 2/1990 | Israel et al. | |
| 5,217,445 A | 6/1993 | Young et al. | |
| 5,716,703 A | 2/1998 | Payne | |
| 6,459,014 B1 | 10/2002 | Chmielewski et al. | |
| 6,620,293 B2 | 9/2003 | Sears et al. | |
| 6,855,134 B2 | 2/2005 | Brooks | |
| 7,056,847 B2 | 6/2006 | Walker et al. | |
| 7,138,561 B2 | 11/2006 | Fuchs et al. | |
| 7,288,167 B2 | 10/2007 | Sears et al. | |
| 7,491,862 B1 | 2/2009 | Besemer et al. | |
| 7,513,973 B2 | 4/2009 | Stoyanov et al. | |
| 7,767,598 B2 | 8/2010 | Schneider et al. | |
| 7,786,341 B2 | 8/2010 | Schneider et al. | |
| 2002/0088581 A1 | 7/2002 | Graef et al. | |
| 2003/0003830 A1 | 1/2003 | Ouederni et al. | |
| 2004/0103970 A1 | 6/2004 | Quederni et al. | |
| 2004/0242106 A1 | 12/2004 | Rabasco et al. | |
| 2005/0008608 A1 | 1/2005 | Parkhurst et al. | |
| 2005/0217809 A1 | 10/2005 | Stephens et al. | |
| 2005/0217811 A1 | 10/2005 | Stephens et al. | |
| 2006/0118255 A1 | 6/2006 | Sears et al. | |
| 2007/0020452 A1 | 1/2007 | Hamed et al. | |
| 2007/0077428 A1 | 4/2007 | Hamed et al. | |
| 2007/0118087 A1 | 5/2007 | Flohr et al. | |
| 2007/0167096 A1 | 7/2007 | Scott | |
| 2008/0177057 A1 | 7/2008 | Bolduc et al. | |
| 2009/0218059 A1* | 9/2009 | Farwaha et al. ............ | 162/164.6 |

FOREIGN PATENT DOCUMENTS

| | | |
|---|---|---|
| DE | 4136540 A1 | 5/1992 |
| EP | 1358894 A1 | 11/2003 |
| EP | 1978140 A1 | 10/2008 |
| JP | 2007135979 A | 6/2007 |

* cited by examiner

*Primary Examiner* — Jacqueline F. Stephens
(74) *Attorney, Agent, or Firm* — Roberts Mlotkowski Safran & Cole P.C.

(57) ABSTRACT

Disclosed herein are nonwoven fibrous structures for use as body fluid acquisition/distribution elements in personal care products. Such structures comprise natural and/or synthetic fibers wherein the fibers have been consolidated by application thereto, and by cross-linking of, a certain type of cross-linkable, vinyl acetate-ethylene (VAE) emulsion copolymer latex binder. The VAE latex binder is one which also comprises an added organic acidulant such as citric acid. Consolidation of the structures with VAE-based binders to which the organic acidulant has been added imparts to the resulting structures the ability to lower the pH of body fluids such as urine passing through the structures. This effect, in turn, provides odor control and skin care benefits to the absorbent articles, e.g., diapers and adult incontinence products, using such structures as acquisition/distribution elements.

33 Claims, No Drawings

ALKALI NEUTRALIZING ACQUISITION AND DISTRIBUTION STRUCTURES FOR USE IN PERSONAL CARE ARTICLES

FIELD

The present development relates to nonwoven fibrous structures which can be used as body fluid acquisition/distribution elements in absorbent personal care products. Such structures are consolidated with a latex binder which imparts to the structure the ability to reduce the pH of alkaline body fluids passing through the structure, thereby reducing odor, bacterial growth and skin irritation.

BACKGROUND

Personal care products in the form of disposable absorbent articles are broadly available. Such products can include, for example, disposable diapers, adult incontinence briefs, panty liners, sanitary napkins, and the like. Such articles are generally worn in contact with or in proximity to the human body and can be used for the collecting and retaining of exuded body fluids.

Typically, personal care products in the form of absorbent articles comprise multiple fluid handling or contacting members or elements. At least one such member will be primarily designed to store liquid, and at least one other member will be primarily designed to acquire and/or distribute liquid.

The storage member used in such products and articles will often comprise super-absorbent material, which is admixed with the traditionally used pulp fiber material. Such super-absorbent materials can absorb many times (e.g., 10 or more times) their own weight in liquid. Modern products employ high concentrations of super-absorbent materials, that is concentrations in excess of 50% of the total weight of the storage member. These products achieve a high absorbing capacity with a very thin storage member and are accordingly typically overall thin products. While super-absorbent materials can store very large amounts of liquid, they are often not able to distribute the liquid from the point of impact to more remote areas of the absorbent article. Further, these types of storage members cannot acquire and absorb liquid as fast as liquid is received by the absorbent article.

Given the foregoing fluid handling characteristics of absorbent article storage members, acquisition/distribution layer (ADL) elements are often also used in absorbent articles. ADLs are members or elements which provide for the interim acquisition of large amounts of liquid and which often also allow for the relatively rapid distribution of that acquired liquid. The ADL thus plays a key role in using the whole absorbent capacity provided by the storage member.

In some instances, an ADL can be a sub-layer in an absorbent article, arranged between a topsheet and an absorbent storage core for holding fluid. The primary function of such an ADL is to transport fluid inputs from the outer surface of the absorbent article, such as a diaper or a feminine hygiene product, to the inner absorbent core, thereby imparting fast strikethrough and low rewet. To achieve these properties, the ADL design is typically a bulky, open-structured, resilient, fibrous nonwoven structure offering good compression recovery regaining its loft quickly after compaction.

Configurations for absorbent article ADLs have historically been nonwoven fibrous structures or webs comprising natural and/or synthetic fibers. These structures can be prepared by such techniques as wet-laying or dry-laying, e.g., air-laying, carding or combinations thereof. Such structures are then typically chemically consolidated or bonded by applying or infusing an emulsion copolymer, i.e., a latex, onto or into the structure and by subsequently curing the latex-containing structure to form the consolidated ADL.

Emulsion copolymers in latex form which have been used in ADL manufacture include styrene-butadiene-rubber (SBR) copolymers, acrylic-based copolymers and copolymers based on vinyl esters such as vinyl acetate. Latex ADL binders of these several types are disclosed, for example, in U.S. Patent Publication Nos. 2004/0242106; 2004/0103970; 2003/0089043 and 2003/0003830.

Body fluids, such as urine, which are acquired by, distributed through, and absorbed and stored by personal care products in the form of absorbent articles are generally alkaline liquids. Such alkaline liquids within the absorbent article can promote bacterial growth and ammonia generation which can, in turn, create problems of odor and skin irritation, i.e., diaper rash, for the wearer of the article. For this reason, pH neutralizing agents are frequently added to the absorbent cores, or even topsheets, of articles such as diapers in an effort to minimize odor and skin irritation problems.

Even if pH lowering additives are present in absorbent article absorbent cores or topsheets, existing commercially available ADL structures which also may be incorporated into such articles do not reduce the alkalinity of body fluids, such as urine, being distributed through such ADL structures. In fact, ADLs which are adhesively bonded using some types of consolidation chemistries may actually exacerbate fluid alkalinity problems. For example, SBR or acrylic emulsion copolymers, when used as ADL binders, require alkaline pH for good machine runnability during nonwoven ADL production. These types of emulsion copolymers are typically supplied at neutral or alkaline pH and often require post-addition of alkali, e.g., ammonia, to achieve good mechanical stability. The very nature of emulsion copolymers of this type renders them ineffective at reducing urine alkalinity, and they can furthermore destabilize if used in the presence of acidulants.

Given the foregoing considerations, it would be advantageous to identify additional types of ADL structures which utilize consolidation/bonding additives that can actually impart a pH lowering/alkalinity neutralizing effect to the ADL structure. ADLs employing such consolidation/bonding chemistry could thus serve to desirably lower the pH/alkalinity of body fluids passing through the ADL before the fluid reaches the absorbent storage core. This, in turn, could eliminate, or at least reduce, the need to incorporate significant amounts of pH/alkalinity control agents into the absorbent article core or topsheet, thereby simplifying the manufacture and converting of such articles.

SUMMARY

In one aspect, the development described herein is directed to a nonwoven fibrous structure for use as a body fluid acquisition/distribution element in a personal care product. Such a structure comprises natural or synthetic fibers, or combinations of these fibers, wherein the fibers have been consolidated by application thereto, and by cross-linking of, a cross-linkable, vinyl acetate-ethylene (VAE) emulsion copolymer latex binder. This VAE latex binder also comprises from about 1.0 wt % to about 5.0 wt % based on total monomer content of the emulsion copolymer of an added organic acidulant such as citric acid. Addition of the organic acidulant allows the resulting structures to lower the pH of body fluids passing through the structure, preferably by at least about 1.2 pH units, to thereby impart odor control and skin care benefits to the absorbent products which utilize such structures.

In another aspect, the development described herein is directed to a personal care product in the form of an infant diaper or an adult incontinence product. Such a personal care product comprises a topsheet, an absorbent fluid storage core and at least one nonwoven fibrous structure of the type hereinbefore described interposed as an acquisition/distribution layer between the topsheet and the absorbent fluid storage core.

In yet another aspect, the development described herein is directed to a process for preparing a nonwoven fibrous structure suitable for use as a body fluid acquisition/distribution element in a personal care product. In the first step of such a process, an aqueous emulsion copolymer latex binder is provided comprising a cross-linkable ethylene-vinyl acetate copolymer which is the emulsion polymerization product of from about 10 to about 25 pphm of ethylene; from about 75 to about 90 pphm of vinyl acetate; and from about 1 to about 10 pphm of additional cross-linkable co-monomers. In the next step of such a process an organic acidulant is added to the aqueous emulsion copolymer latex binder in an amount of from about 1.0 to about 5.0 weight percent based on total weight of monomers in the emulsion copolymer. In the next step of the process, the acidulant-containing aqueous emulsion copolymer latex binder is contacted with a nonwoven fibrous structure comprising wet-laid or dry-laid natural and/or synthetic fibers to form a latex binder-containing nonwoven fibrous structure. In the final step of the process, the latex binder-containing nonwoven fibrous structure is subjected to curing conditions sufficient to cross-link the copolymer and to thereby form an acidulant-containing, consolidated nonwoven fibrous structure.

DETAILED DESCRIPTION

Described herein are nonwoven fibrous structures which are useful as fluid acquisition/distribution layers (ADL) in body-fluid absorbing elements of personal care products. These fibrous structures are consolidated and strengthened by application thereto, and curing of, a vinyl acetate/ethylene (VAE) latex binder. Added to the latex binder is an organic acidulant which is carried by the latex into the fibrous structure treated with this latex binder. The fibrous structures herein, the VAE binder and the organic acidulants used, along with the personal care products which utilize such ADL structures, are described in greater detail hereinafter.

Nonwoven Fibrous Structures

Nonwoven fibrous structures are well known and conventionally used in personal care absorbent articles such as infant diapers, adult incontinence products and feminine hygiene articles. A nonwoven fibrous structure is a manufactured sheet, web, batt or mass of directionally or randomly oriented fibers, generally bonded together by friction and/or cohesion and/or adhesion. Such structures can be formed by any one of the conventional techniques for depositing or arranging fibers in a web or layer. Such techniques include wet laying, air-laying, carding, garnetting, etc, or combinations of such techniques.

The fibers used to form the nonwoven fibrous structures herein can be of natural or synthetic origin. Combinations of natural and synthetic fibers may also be used in the nonwoven structures useful herein. The fibers forming the structures may be staple or continuous filaments or can be formed in situ.

Examples of natural fibers which can be used in the nonwoven fibrous structures herein include, but are not limited to, vegetable fibers such as cellulose, cotton, flax, linen, and hemp. Natural fibers are typically shorter than their synthetic counterpart and can range from about 1.5 to about 7 mm in length, more preferably from about 2.5 to about 5 mm in length. The thickness of natural fibers is quoted as "coarseness" due to their irregular morphology. Preferred values for coarseness are between about 2 g per 10000 meters and about 10 g per 10000 meters and most preferably between about 3 and about 5 g per 10000 meters. A value of 3.4 g per 10000 meters equates to 3.4 decitex.

Preferred natural fibers are cellulose fibers which can be supplied in the form of fluff pulp. The term "fluff pulp" refers to a pulp prepared by chemical, mechanical or combined chemical and mechanical treatment, usually bleached, and known for use as an absorbent medium, for example in disposable absorbent articles.

In one embodiment, cellulose fibers useful in the nonwoven fibrous structures which can serve as acquisition/distribution layers comprise chemically stiffened cellulose fibers. As used herein, the term "chemically stiffened fibers" means any fibers which have been stiffened by chemical means to increase stiffness of the fibers and to possibly also impart curl or twist thereto under both dry and aqueous conditions. Such means include the addition of chemical stiffening agents which, for example, coat and/or impregnate the fibers. Such means also include the stiffening of the fibers by altering the chemical structure of the fibers themselves, e.g., by cross-linking polymer chains. Use of chemically stiffened and curled cellulose fibers in acquisition/distribution structures is more fully described in U.S. Pat. No. 5,217,445 and the several references cited therein. This '445 U.S. patent is incorporated by reference herein in its entirety.

Synthetic fibers may also be used to form the nonwoven fibrous structures used in the ADLs of the personal care products herein. Synthetic, i.e., man-made, fibers can be derived, for example, from natural fibers or mineral sources. Examples of synthetic fibers which are derived from natural fibers include, but are not limited to, rayon and lyocell, both of which are derived from cellulose. Synthetic fibers derived from mineral sources include, but are not limited to, polyolefin fibers such as polypropylene fibers or polyethylene fibers, polyester fibers, and polyamide fibers, all of which are derived from petroleum. Preferred synthetic fibers for use in the ADL structures herein are polyester fibers, such as polyethylene terephthalate ("PET") fibers.

The synthetic fibers useful in the ADL structures herein can range from about 4 to about 25 mm in length, more preferably from about 3 to about 12 mm in length and most preferably from about 5 to about 6 mm in length. The synthetic fibers can typically vary in thickness between about 3 and about 30 decitex. Preferred thickness for useful synthetic fibers is between about 4 and about 12 decitex, most preferably between about 6 and about 8 decitex.

In one embodiment, the synthetic fibers useful in the ADL structures herein will exhibit a crimp, preferably a spiral-crimp. As used herein, a spiral-crimp is any three-dimensional crimp and preferably one wherein the fibers substantially assume a helical shape. Without wishing to be bound by theory, it is believed that the spiral crimping of fibers is very beneficial for their liquid acquisition and distribution behavior. It is assumed that the spiral crimp increases the void space in an acquisition/distribution member formed by such fibers. Often, an absorbent article, when being worn, is exposed to a certain pressure exerted by the wearer, which potentially decreases the void space in the ADL member. Having good permeability and sufficient void space available are important for good liquid distribution and transport.

The synthetic fibers useful in the ADL structures herein can vary in their level of crimp, with crimp being classified as either straight, medium or high. Higher crimp allows ease of fiber separation but slows forming capacity and line speed since their elastic character allows the fibers to "bounce", for example, inside the head assembly of an airlaying apparatus. Medium crimp fibers are the preferred choice for structures made using an air-laying process, offering a compromise between ease of separation and line speed. Preferred crimp values for synthetic fibers used herein are between about 6 and about 20 crimps per inch, more preferably between about 8 and about 12 crimps per inch.

In one embodiment, the nonwoven fibrous structures useful as ADLs herein can comprise combinations, i.e., blends, of both natural and synthetic fibers. Such blends may comprise at least about 10 to about 90 weight % of the synthetic fibers with the remaining weight % portion of the blend being natural fibers. More preferred is a blend of from about 40 to about 60 weight % of synthetic fibers and from about 60 to about 40 weight % of natural fibers. ADL structures comprising blends of both natural and synthetic fibers are more fully described in U.S. Patent Publication No. 2007/0167096. This '096 U.S. patent publication is incorporated herein by reference in its entirety.

VAE Latex Binder

The nonwoven fibrous structures as hereinbefore described are consolidated by applying thereto, and by then subsequently curing, a certain selected type of latex binder composition. As is well known, latex binders are applied to a nonwoven structure generally in an aqueous liquid form that accumulates in fiber intersections. After curing, the binder forms a coherent polymeric film that consolidates and stabilizes the nonwoven structure. When the nonwoven is stressed (e.g., by compression), the polymeric film resists that stress so the fibers comprising the nonwoven are inhibited from moving.

The latex binders used to prepare the chemically bonded, nonwoven fibrous structures useful herein as ADLs are those prepared by the emulsion copolymerization of vinyl acetate (VA) and ethylene (E). In such VAE copolymers, the vinyl acetate monomer will generally comprise from about 75 to about 90 pphm (parts per hundred based on total monomers) and ethylene will generally comprise from about 10 to about 25 pphm. More preferably in such emulsion copolymers, the vinyl acetate monomer will generally comprise from about 80 to about 90 pphm and ethylene will generally comprise from about 10 to about 20 pphm.

The VAE emulsion copolymer latex binder used herein is generally a crosslinkable emulsion copolymer. By "crosslinkable" it is meant that the copolymer is capable of undergoing crosslinking, either by a self-crosslinking mechanism, or by the incorporation of at least one functional monomer into the copolymer backbone which can undergo a post-polymerization crosslinking reaction to form crosslinks.

In a preferred embodiment, the emulsion copolymer comprises, in addition to vinyl acetate and ethylene co-monomers, from about 1 to about 10 pphm of at least one additional type of functional cross-linking co-monomer. More preferably, the least one additional type of functional cross-linking co-monomer will comprise from about 2 to about 8 pphm of the emulsion copolymer forming the binder latex.

The crosslinking monomers used herein can include co-monomers comprising cross-linkable N-methylol groups or their derivatives which are etherified with C1-C6 alkanols. These derivatives include N-methylol amides of acrylic acid and methacrylic acid (such as N-methylol acrylamide and N-methylol methacrylamide), N-methylol allyl carbamate, iso-butoxy methyl acrylamide, n-butoxy methyl acrylamide, and mixtures of such cross-linking co-monomers. Other possible cross-linking co-monomers include those disclosed in U.S. Pat. No. 7,056,847, which is incorporated herein by reference.

In addition to the cross-linking co-monomer(s) described above, the emulsion copolymer which forms the binder latex compositions used herein can contain a variety of additional optional co-monomer types. Such additional optional co-monomers can include, for example, additional vinyl esters of aliphatic carboxylic acids containing up to about 12 carbon atoms; dialkyl esters of maleic and fumaric acid containing about 1 to about 8 carbon atoms in each alkyl group; and C1-C8 alkyl acrylates and methacrylates. Other additional optional co-monomers for possible inclusion in the emulsion copolymer used herein are disclosed in the above-referenced U.S. Pat. No. 7,056,847.

The copolymer emulsion latex binder can be prepared using conventional batch, semi-batch or semi-continuous emulsion polymerization procedures. Generally, the monomers are polymerized in an aqueous medium under ethylene pressure in the presence of a redox initiator system and at least one emulsifying agent useful as a dispersing agent or emulsion stabilizer. Processes suitable for the emulsion polymerization of VAE emulsion copolymers are described in U.S. Pat. No. 5,540,987, incorporated herein by reference.

If a batch process is used, the vinyl acetate and any optional non-functional monomers are suspended in water under ethylene pressure and are thoroughly agitated while being gradually heated to polymerization temperature. The homogenization period is followed by a polymerization period during which the initiator and functional monomer(s), such as N-methylol acrylamide, are added incrementally or continuously. The functional monomer is added slowly to the reaction to minimize its homopolymerization, and instead promote incorporation of the functional monomer into the polymer backbone. If the slow addition procedure is employed, the vinyl acetate and any optional co-monomers are added gradually throughout the polymerization reaction.

In either case, the polymerization is performed at temperatures from about 25° C. to about 80° C., preferably from about 35° C. to about 60° C., for sufficient time to achieve a low residual monomer content, e.g., from 0.5 to about 10 hours, preferably from about 2 to about 6 hours, to produce a latex having less than 1 percent, preferably less than 0.2 weight percent, free monomer. A lower reaction temperature range for the polymerization allows for a more controlled conversion rate, allowing for the incorporation of a higher level of cross-linking monomer.

The initiator system is generally a redox system. Redox systems using persulfate or peroxide initiators along with a reducing agent are preferred. Peroxide initiators, and most preferably tert-butyl hydrogen peroxide (tBHP), may be used to initiate polymerization. One particularly preferred initiator system comprises a hydrophobic hydroperoxide, in amounts of between about 0.05 and about 3 percent by weight, preferably between about 0.1 and about 1 percent by weight based on the total amount of the emulsion, in combination with ascorbic acid, in amounts of from about 0.05 to about 3 percent by weight, preferably from about 0.1 to about 1 percent by weight, based on the total amount of the emulsion. The redox initiator system is slow-added during the polymerization.

To control the generation of free radicals, a transition metal often is incorporated into the redox system, and such metals can include an iron salt, e.g., ferrous and ferric chloride and ferrous ammonium sulfate. The use of transition metals and levels of addition to form a redox system for polymerization mediums are well-known.

The polymerization is generally carried out at a pH of between about 2 and about 7, more preferably between about 3 and about 5. In order to maintain the pH range, it may be useful to work in the presence of customary buffer systems, for example, in the presence of alkali metal acetates, alkali metal carbonates, or alkali metal phosphates.

Useful dispersing agents/stabilizers are emulsifiers, surfactants, and protective colloids generally used in emulsion polymerization, or a combination thereof. The emulsifiers can be anionic, cationic or nonionic surface active compounds, as known in the art.

Suitable anionic emulsifiers are, for example, alkyl sulfonates, alkylaryl sulfonates, alkyl sulfates, sulfates of hydroxyalkanols, alkyl and alkylaryl disulfonates, sulfonated fatty acids, sulfates and phosphates of polyethoxylated alkanols and alkyphenols, as well as esters of sulfosuccinic acid. Suitable cationic emulsifiers are, for example, alkyl quaternary ammonium salts, and alkyl quaternary phosphonium salts. Examples of suitable non-ionic emulsifiers are the addition products of about 5 to about 50 moles of ethylene oxide adducted to straight-chained or branch-chained alkanols with about 6 to about 22 carbon atoms, or alkylphenols, of higher fatty acids, or higher fatty acid amides, or primary and secondary higher alkyl amines; as well as block copolymers of propylene oxide with ethylene oxide and mixtures thereof.

The amount of emulsifying agent used is generally from about 1 to about 10, more preferably from about 2 to about 8, weight percent of the monomers used in the polymerization. The emulsifying agent may be added in its entirety to the initial charge, or a portion of the emulsifier, e.g., from about 25 to about 90 percent thereof, can be added continuously or intermittently during polymerization.

Various protective colloids may also be used in addition to the emulsifiers described above. Suitable colloids include polyvinyl alcohol (PVA), partially acetylated polyvinyl alcohol, e.g., up to 50 percent acetylated PVA, casein, hydroxyethyl starch, carboxymethyl cellulose, gum arabic, and the like, as known in the art of synthetic emulsion polymer technology. In general, these colloids are used at levels of from about 0.05 to about 4 percent by weight, based on the total emulsion.

The polymerization reaction is generally continued until the residual vinyl acetate monomer content is below about 1 percent, preferably less than about 0.2 percent. The completed reaction product is then allowed to cool to about room temperature, while sealed from the atmosphere.

The emulsions are produced and used at relatively high solids contents, e.g., between about 35 to about 60 weight percent, preferably between about 50 to about 55 percent, although they may be diluted with water as desired. Preferably the viscosity of the emulsion at 50 percent solids is less than about 500 cps.

The particle size of the latex so produced can be regulated by the quantity of nonionic, cationic or anionic emulsifying agent or protective colloid employed. To obtain smaller particles sizes, greater amounts of emulsifying agents are used. As a general rule, the greater amount of the emulsifying agent employed, the smaller the average particle size of the copolymer in the latex emulsion. The VAE-based copolymer in the latex emulsion will generally have a glass transition temperature, Tg, in the range of from about −10° C. to about +30° C., and more preferably between about −5° C. and about +15° C.

Organic Acidulant

After preparation of the latex binder composition as hereinbefore described, and before the latex binder is contacted with the nonwoven fibrous structure, an organic acidulant is added to the aqueous VAE-based copolymer-containing latex binder. The organic acidulant is the component which is carried by the binder latex into the fibrous nonwoven structures herein and which imparts pH lowering capability to such structures. Such organic acids are generally those having a pKa in water ranging from about 2 to about 7.

Any relatively inert organic acid compound which can safely be incorporated or introduced into structures suitable for use in proximity to the human body can be used as the organic acidulant. Preferably, the organic acidulant can be an aliphatic, saturated, mono- or poly-carboxylic acid compound having from 2 to about 12 carbon atoms. Examples of such organic acids include oxalic acid, succinic acid, adipic acid, glutaric acid, tartaric acid and citric acid. Citric acid is the most preferred organic acidulant.

Organic acids which are used as the acidulant do not react with the VAE-based copolymer or co-monomeric precursors thereof. The organic acidulant furthermore should not chemically react with any components of the nonwoven fibrous structure into which the acidulant-containing latex binder is introduced. The organic acids suitable as acidulants can, however, act as catalysts which promote the cross-linking of the cross-linkable, VAE-based copolymer of the latex binder. For this reason, addition of the organic acidulant to the latex binder composition might, in some instances, serve to eventually de-stabilize the binder emulsion by promoting premature cross-linking of the copolymer of the binder.

Given the foregoing considerations, the organic acidulant should preferably be added to the VAE-based copolymer latex binder within several hours before, e.g., within 5 hours before, or even within 2 hours before, the latex binder is to be contacted with the nonwoven fibrous structure. The organic acidulant will generally be added in this manner to the VAE-based copolymer-containing binder latex in an amount of from about 1.0 wt % to about 5.0 wt % based on total monomer content of VAE-based copolymer. More preferably, the organic acidulant can be added to the VAE-based copolymer-containing binder latex in an amount of from about 1.0 wt % to about 2.0 wt %, based on total monomer content of the VAE-based copolymer.

The amount of acidulant added to the latex binder will preferably be effective to impart to the nonwoven fibrous structure the capacity to lower the pH of body fluid within that structure to the extent of at least about 1.2 pH units. More preferably, the acidulant will be added in an amount sufficient to impart at least about 2.0 units of pH lowering capacity to the nonwoven structure.

Structure Preparation

The acidulant-containing latex binder compositions hereinbefore described are used to bind fibers together in the nonwoven fibrous structures also hereinbefore described. The latex binder compositions are thus used in a manufacturing process which produces structures in the form of a wetlaid or airlaid and chemically-bonded web, as opposed to mechanically tangled or thermally bonded webs. Alternatively, the acidulant-containing latex binder compositions can be used to post-treat and further strengthen mechanically tangled or thermally bonded webs which have been pre-formed in the absence of a chemical bonding agent.

In the manufacturing process for chemically bonded structures, the latex binder composition can be applied to the nonwoven fibrous structures described herein by any means known in the art, such as print, foam, saturate, coating, and spraying application. The binder-containing structure can then be cured, i.e., dried, on steam cans or in ovens as currently practiced in the production of nonwoven rolled goods.

Binder add-on levels for nonwoven fibrous structures herein can be from about 5 to about 40 weight percent, more preferably from about 10 to about 30 weight percent. Most preferred is the spray application of the latex binder composition to the fibrous structure in combination with drying and curing of the resulting web using heated ovens.

Personal Care Absorbent Articles

The acidulant-containing, chemically bonded nonwoven fibrous structures described herein are useful as fluid acquisition/distribution elements in personal care products designed to absorb alkaline body fluids such as infant or adult urine. Thus the structures herein are useful in applications wherein wet integrity or resiliency are important, such as in, for example, infant diapers, adult incontinence articles and devices and feminine hygiene products.

The use of nonwoven fibrous structures as body fluid acquisition/distribution layers in personal care article such as diapers is well known. Structures which perform this function are described, for example, in U.S. Pat. Nos. 5,217,455; 5,716,703; 7,138,561; 7,767,598; and 7,786,341, all of which patents are incorporated herein by reference. The nonwoven structures herein can function as ADLs in analogous manner to the ADLs in such known contexts. However, in addition to the fluid handling properties which such structures are expected to exhibit, the nonwoven fibrous structures herein perform the additional beneficial function of lowering the pH of alkaline body fluids being handled by such structures.

Typically, personal care articles which can utilize the nonwoven fibrous structures described herein as ADLs can be in the form of an infant diaper or an adult incontinence product. Such products generally comprise a fluid pervious topsheet, an absorbent fluid storage core and at least one nonwoven fibrous structure of the type described herein interposed as an acquisition/distribution layer between the topsheet and the absorbent fluid storage core. These three elements are, of course, in fluid communication with each other such that body fluid striking the article passes through the topsheet and is acquired by the ADL structure. The ADL element then transports and distributes acquired fluid to the absorbent storage core wherein it is absorbed and held until the absorbent article is removed from the wearer and disposed of.

Use of the acidulant-containing, VAE-based latex binders described herein to consolidate nonwoven fibrous structures serves to provide acquisition/distribution elements especially suitable for alkaline urine pH lowering in adult incontinence products. The issues associated with alkaline urine (odor, skin irritation, bacterial growth) are more prevalent in the elderly. This is because the elderly consume more antacids, bone-strengthening supplements, and other medicines that can raise the pH of adult urine in comparison with relatively lower pH infant urine.

EXAMPLES

The preparation of pH-lowering, chemically bonded, nonwoven fibrous structures as described herein, as well as the pH lowering effect which such structures can exhibit, are illustrated by the following examples:

Example I

A chemically bonded, airlaid nonwoven substrate is prepared on M&J Fibertech (now Neumag Denmark) airlaid pilot web-forming apparatus. Such an airlaid substrate is prepared from Weyerhaeuser NB416 fluff pulp which is commercially available from Weyerhaeuser Company.

The airlaid nonwoven substrate is produced utilizing machine line speeds of 50 meters per minute with an exit sheet temperature of 155° C. The airlaid basesheet conditions consist of a target basis weight of 55 grams per square meter (gsm) and a caliper range of 0.8-1.1 millimeters (mm). Latex binder add-on targets 14 percent by weight of the final nonwoven and is achieved via spray-application of the binder latex at dilution solids of 12 to 13 percent.

The latex binder emulsion utilized is DUR-O-SET Elite® 33, a self-crosslinking vinyl acetate/ethylene (VAE) emulsion copolymer which is commercially available from Celanese Emulsions. This VAE copolymer has a Tg of +10° C. Prior to spray-on, a 10% citric acid solution is added as an acidulant to the VAE copolymer emulsion in an amount sufficient to provide a citric acid concentration in the emulsion of 2.0 wt % based on total monomer content in the copolymer emulsion.

The resulting chemically bonded nonwoven substrate can be converted into nonwoven structures which are suitable for use as acquisition/distribution layers in personal care absorbent articles such as infant diapers and adult incontinence products. Such structures advantageously release citric acid into alkaline body fluid passing through such structures. The resulting lowering of the pH of the body fluid serves to inhibit odor and bacterial growth within the absorbent articles as well as to minimize skin irritation for the wearer of the article.

Example II

To simulate an ADL nonwoven substrate which has been consolidated with a latex binder, Whatman CR-4 paper is treated with various emulsion copolymer latex compositions and cured. Each nonwoven sample so prepared is then tested for its urine pH lowering effect by contacting each treated nonwoven sample with synthetic urine and by then measuring the pH drop in the urine as a result of that contact.

The synthetic urine used in the testing is made from 18.0 grams of NaCl in 2 liters of deionized water. The liquid is then adjusted to a pH of 8.5 with aqueous ammonia. The synthetic urine so prepared has a specific gravity of 1.005 g/cm3 and a surface tension of 52 dynes/cm.

Several binder formulations are prepared for use in treating the Whatman paper substrates. These formulations include a VAE emulsion copolymer (Elite® 33) with or without additives and a styrene-butadiene rubber (SBR) emulsion copolymer (Genflo® 3060) with or without various additives. These binder formulations and their characteristics are shown in Table 1.

TABLE 1

Binder Formulations

| Binder Sample No. | Binder Type | Binder pH | Binder Stability (% grit) (200 mesh) |
|---|---|---|---|
| A | Elite ® 33 VAE Binder as is | 4.29 | 0.0019 |
| B | Elite ® 33 VAE Binder + 2.0 pphm Citric Acid | 2.95 | 0.0024 |
| C | SBR Binder as is | 7.92 | 0.0062 |
| D | SBR Binder + Aqueous Ammonia | 8.5 | 0.0031 |
| E | SBR Binder + 2.0 pphm Citric Acid | 4.26 | Coagulated |
| F | SBR Binder + 1.0 pphm Citric Acid | 6.0 | 0.0084 (gritty) |

The nonwoven substrates used for testing are prepared, in one instance, from untreated Whatman CR-4 paper and, in other instances, from Whatman CR-4 paper which has been pad-saturated with the various binder formulations to be tested, oven-dried at 150° C. for 2 minutes and then conditioned overnight at constant temperature and humidity before being tested. The binder formulations are added onto the nonwoven substrate immediately after the additive has been combined with the base formulation. The characteristics of the several nonwoven substrates which are prepared for testing are shown in Table 2.

TABLE 2

Nonwoven Substrates Based on Whatman Paper

| Binder Sample No. | Binder Type | Binder Add-On (wt %) | Basis Weight (g/m$^2$) |
|---|---|---|---|
| None | None | 0 | n/a |
| A | VAE | 24.6 | 135.67 |
| B | VAE + Citric Acid | 25.0 | 135.8 |
| C | SBR | 25.0 | 135.86 |
| D | SBR + Ammonia | 24.8 | 135.5 |
| E | SBR + 2.0 Citric Acid | n/a | n/a |
| F | SBR + 1.0 Citric Acid | 24.9 | 135.52 |

To determine the pH lowering effect of each of the Table 2 substrates, each substrate is formed into a cone-shaped filter, and 100 milliliters of the pH 8.5 synthetic urine is poured through the filter. The pH of the urine samples after each has passed through a substrate sample being evaluated is measured. From these measurements, the drop in urine pH imparted to the test liquid by each substrate type tested can be determined. Test results are shown in Table 3.

TABLE 3

Urine pH Drop When Poured Through Nonwoven Substrates

| Binder | | Urine pH After Filtering | | Average |
|---|---|---|---|---|
| Sample No. | Binder Type | Sample 1 | Sample 2 | pH Drop |
| None | None | 8.23 | 8.31 | 0.23 |
| A | VAE | 7.59 | 7.62 | 0.90 |
| B | VAE + Citric Acid | 5.31 | 5.47 | 3.11 |
| C | SBR | 7.97 | 7.74 | 0.65 |
| D | SBR + Ammonia | 8.16 | 8.09 | 0.38 |
| E | SBR + 2.0 Citric Acid | n/a | n/a | n/a |
| F | SBR + 1.0 Citric Acid | 7.54 | 7.49 | 0.99 |

The data in the foregoing tables demonstrate that addition of an acidulant such as citric acid to a VAE latex binder can impart to a nonwoven substrate consolidated with such a binder the ability to significantly lower the pH of synthetic urine passing through the substrate. The data further indicate that nonwoven substrates consolidated with an SBR latex binder, especially in the presence of added ammonia stabilizer, do not significantly lower the pH of synthetic urine passing therethrough. Attempts to add an acidulant such as citric acid to the SBR latex binder either cause the SBR latex binder to coagulate or do not impart significant pH lowering effect to the structure consolidated with the citric acid-containing SBR latex binder.

While the illustrative embodiments of the disclosure have been described with particularity, it will be understood that various other modifications will be apparent to and can be readily made by those skilled in the art without departing from the spirit and scope of the disclosure. Accordingly, it is not intended that the scope of the claims appended hereto be limited to the examples and descriptions set forth herein but rather that the claims be construed as encompassing all the features of patentable novelty which reside in the present disclosure, including all features which would be treated as equivalents thereof by those skilled in the art to which the disclosure pertains.

What is claimed is:

1. A nonwoven fibrous structure for use as a body fluid acquisition/distribution element in a personal care product, said structure comprising natural or synthetic fibers, or combinations of said fibers, which fibers have been consolidated by application thereto, and by cross-linking of, a cross-linkable, vinyl acetate-ethylene (VAE) emulsion copolymer latex binder, said latex binder comprising from about 1.0 wt % to about 5.0 wt % based on total monomer content of said copolymer of an organic acidulant.

2. The nonwoven fibrous structure according to claim 1, wherein the synthetic fibers comprise polyester fibers.

3. The nonwoven fibrous structure according to claim 1 wherein the natural fibers comprise fluff pulp fibers.

4. The nonwoven fibrous structure according to claim 3 wherein the fluff pulp fibers comprise cellulosic fluff pulp fibers.

5. The nonwoven fibrous structure according to claim 1 wherein the fibers in the structure comprise a blend of from about 40 to about 60 weight % of synthetic fibers and from about 40 to about 60 weight % of natural fibers.

6. The nonwoven fibrous structure according to claim 1 wherein the synthetic fibers are crimped.

7. The nonwoven fibrous structure according to claim 1 wherein the fibrous structure comprises an airlaid, carded, or airlaid and carded web.

8. The nonwoven fibrous structure according to claim 1 wherein the cross-linkable VAE emulsion copolymer in the latex binder comprises from about 75 to about 90 pphm of vinyl acetate; from about 10 to about 25 pphm of ethylene and from about 1 to about 10 pphm of at least one additional cross-linkable co-monomer.

9. The nonwoven fibrous structure according to claim 8 wherein said at least one additional cross-linkable co-monomer comprises cross-linkable N-methylol groups or their derivatives which are etherified with $C_1$-$C_6$ alkanols.

10. The nonwoven fibrous structure according to claim 9 wherein the additional cross-linkable co-monomers are derived from N-methylol amides of acrylic acid and methacrylic acid.

11. The nonwoven fibrous structure according to claim 1 wherein the crosslinked copolymer of the latex binder has a glass transition temperature, $T_g$, in the range from about −10° C. to about +30° C.

12. The nonwoven fibrous structure according to claim 1 wherein the cross-linkable emulsion copolymer latex binder comprises as a stabilizer at least one emulsifier which is an anionic emulsifier and/or a nonionic emulsifier.

13. The nonwoven fibrous structure according to claim 1 wherein the organic acidulant in the latex binder is a mono- or poly-carboxylic acid having from about 2 to about 12 carbon atoms and a pKa in water of from about 2 to about 7.

14. The nonwoven fibrous structure according to claim 13 wherein the organic acidulant in the latex binder is selected from oxalic acid, succinic acid, adipic acid, glutaric acid, tartaric acid, citric acid, and combinations thereof.

15. The nonwoven fibrous structure according to claim 13 wherein the organic acidulant is citric acid.

16. A personal care product in the form of an infant diaper or an adult incontinence product, wherein said personal care product comprises a topsheet, an absorbent fluid storage core and at least one nonwoven fibrous structure according to claim 1 interposed as an acquisition/distribution layer between said topsheet and said absorbent fluid storage core.

17. The nonwoven fibrous structure according to claim 1, which comprises 5 to 40 wt % of said cross-linkable VAE emulsion copolymer latex binder.

18. A nonwoven fibrous structure for use as a body fluid acquisition/distribution element in a personal care product, said structure comprising natural or synthetic fibers, or combinations of said fibers, which fibers have been consolidated by application thereto, and cross-linking of, a cross-linkable vinyl acetate-ethylene (VAE) emulsion copolymer latex binder, said latex binder comprising an organic acidulant in an amount which is effective to lower the pH of body fluid which passes through said structure to the extent of at least about 1.2 pH units.

19. A process for preparing a nonwoven fibrous structure suitable for use as a body fluid acquisition/distribution element in a personal care product, which process comprises:
   (a) providing an aqueous emulsion copolymer latex binder comprising an cross-linkable ethylene-vinyl acetate copolymer which is the emulsion polymerization product of from about 10 to about 25 pphm of ethylene; from about 75 to about 90 pphm of vinyl acetate; and from about 1 to about 10 pphm of at least one additional cross-linkable co-monomer;
   (b) adding to said aqueous emulsion copolymer latex binder from about 1.0 to about 5.0 weight percent based on total weight of monomers in said emulsion copolymer of an organic acidulant;
   (c) contacting said acidulant-containing aqueous emulsion copolymer latex binder with a nonwoven fibrous structure comprising wet-laid or dry-laid natural and/or synthetic fibers to form a latex binder-containing nonwoven fibrous structure; and thereafter
   (d) subjecting said latex binder-containing nonwoven fibrous structure to curing conditions sufficient to cross-link said copolymer and to thereby form an acidulant-containing, consolidated nonwoven fibrous structure.

20. The process according to claim 19 wherein the synthetic fibers of the nonwoven fibrous structure comprise polyester fibers.

21. The process according to claim 19 wherein the natural fibers of the nonwoven fibrous structure comprise fluff pulp fibers.

22. The process according to claim 21 wherein the nonwoven fibrous structure fibers comprise cellulosic fluff pulp fibers.

23. The process of claim 19 wherein the fibers in the nonwoven fibrous structure comprise a blend of from about 40 to about 60 weight % of synthetic fibers and from to about 40 to about 60 weight % of natural fibers.

24. The process according to claim 19 wherein the synthetic fibers of the nonwoven fibrous structure are crimped.

25. The process according to claim 19 wherein the nonwoven fibrous structure comprises an airlaid, carded, or airlaid and carded web.

26. The process according to claim 19 wherein the additional cross-linkable co-monomers of the ethylene-vinyl acetate copolymer comprise cross-linkable N-methylol groups or their derivatives which are etherified with $C_1$-$C_6$ alkanols.

27. The process according to claim 26 wherein the additional cross-linkable co-monomers are derived from N-methylol amides of acrylic acid and methacrylic acid.

28. The process according to claim 19 wherein the crosslinked copolymer of the latex binder has a glass transition temperature, $T_g$, in the range from about $-10°$ C. to about $+30°$ C.

29. The process according to claim 19 wherein the cross-linkable emulsion copolymer latex binder comprises as a stabilizer at least one emulsifier which is an anionic emulsifier and/or a nonionic emulsifier.

30. The process according to claim 19 wherein the organic acidulant which is added to the latex binder is a mono- or poly-carboxylic acid having from about 2 to about 12 carbon atoms and a pKa in water of from about 2 to about 7.

31. The process according to claim 30 wherein the organic acidulant which is added to the latex binder is carboxylic acid selected from oxalic acid, succinic acid, adipic acid, glutaric acid, tartaric acid, citric acid, and combinations thereof.

32. The process according to claim 30 wherein the organic acidulant is citric acid.

33. A nonwoven fibrous structure for use as a body fluid acquisition/distribution element in a personal care product, said structure comprising natural or synthetic fibers, or combinations of said fibers, which fibers have been consolidated by application thereto, and by cross-linking of, a cross-linkable, vinyl acetate-ethylene (VAE) emulsion copolymer latex binder, said latex binder comprising from about 1.0 wt % to about 5.0 wt % based on total monomer content of said copolymer of an organic acidulant in admixture therewith.

* * * * *